(12) United States Patent
Ellman et al.

(10) Patent No.: US 8,321,031 B1
(45) Date of Patent: Nov. 27, 2012

(54) RADIO-FREQUENCY TREATMENT OF SKIN TISSUE WITH TEMPERATURE SENSING

(75) Inventors: Alan G. Ellman, Oceanside, NY (US); Jon C. Garito, Oceanside, NY (US)

(73) Assignee: Ellman International, Inc, Oceanside, NY (US)

( * ) Notice: Subject to any disclaimer, the term of this patent is extended or adjusted under 35 U.S.C. 154(b) by 1262 days.

(21) Appl. No.: 12/012,447

(22) Filed: Feb. 4, 2008

(51) Int. Cl.
*A61F 7/00* (2006.01)

(52) U.S. Cl. ............... 607/101; 607/100; 607/102

(58) Field of Classification Search ............ 607/102, 607/100, 101
See application file for complete search history.

(56) References Cited

U.S. PATENT DOCUMENTS

| | | | |
|---|---|---|---|
| 6,039,734 A * | 3/2000 | Goble | 606/41 |
| 6,432,105 B1 * | 8/2002 | Ellman et al. | 606/48 |
| 6,592,580 B1 * | 7/2003 | Stockert | 606/41 |
| 7,163,336 B2 * | 1/2007 | Blakeley, III | 374/142 |
| 2002/0188284 A1 * | 12/2002 | To et al. | 606/15 |
| 2004/0111087 A1 * | 6/2004 | Stern et al. | 606/41 |
| 2006/0259102 A1 * | 11/2006 | Slatkine | 607/88 |

* cited by examiner

*Primary Examiner* — Roy Gibson
*Assistant Examiner* — Jared W Pike
(74) *Attorney, Agent, or Firm* — Ganz Law, P.C.

(57) ABSTRACT

A radio-frequency electrode and handpiece that is specially configured to provide a reasonably uniform electric field distribution at the skin surface of a patient being treated to improve the skin appearance. Harmful burning is avoided by sensing and displaying skin and electrode temperature. Continuous electrode contact and electrode motion relative to the skin is achieved by providing a rolling cap over a dome-shaped electrode, and by spring biasing the electrode for up and down motion, and by providing side-to side motion of the electrode manually or by motor.

2 Claims, 6 Drawing Sheets

RADIO-FREQUENCY TREATMENT OF SKIN TISSUE WITH TEMPERATURE SENSING

This invention relates to apparatus and a procedure for treating skin tissue using non-ablative radio-frequency energy. It also relates to monopolar and bipolar electrodes for use in such procedures.

BACKGROUND OF THE INVENTION

Our prior U.S. Pat. No. 6,432,105B1, the contents of which are herein incorporated by reference, describes a novel electrosurgical instrument, in particular a bipolar electrosurgical instrument, that is configured for use in minimally invasive surgery (MIS) and other electrosurgical procedures for, for example, in-body orthopedic treatments. The instrument is constructed with a single rigid end as a bipolar electrode comprising spaced rounded electrodes separated by an electrically-insulated strip. When energized, a bipolar discharge is generated mainly between the bare edges of the electrode segments adjoining the electrically-insulated strip.

In our copending application Ser. No. 11/709,672, filed Feb. 23, 2007, the contents of which are herein incorporated by reference, we describe an electrode configuration and procedure for use for topical application to the tissue surface or skin of a patient for the non-ablative treatment of periorbital rhytides and midface laxity or in general removal of wrinkles or other cosmetic skin tightening procedures to improve the appearance of skin tissue.

In this radio-frequency (RF) non-ablative tissue surface treatment, it is desirable to raise the tissue temperature to about 55-65° C. to affect underlying skin collagen to tighten the surface tissue, being careful to avoid overheating the skin tissue possibly causing burns and residual scarring. To achieve this result, this prior application describes the use of specially configured electrodes to provide a reasonably uniform electric field distribution at the skin surface, pre-applying to the skin a thermal gel, a known thermally and electrically-conductive material, to help cool the surface, using low RF power, relying on the natural cooling provided by a highly conductive electrode material, and continuously manually moving the activated electrode while in contact with the skin.

SUMMARY OF THE INVENTION

An object of the present invention is to employ RF energy for skin conditioning but with non-ablative electrodes specially configured to increase the temperature of skin tissue to reduce skin conditions that impair the beauty of natural healthy skin and without requiring external cooling or producing skin damage, such as by burning.

In accordance with a feature of the invention, a dual electrode scheme is employed to provide a reasonably uniform electric field distribution at the skin surface being treated. In a preferred embodiment, the dual electrodes comprise two side-by-side completely separated dome or ball shaped electrodes. Each can be connected to one of the two terminals of the source electrosurgical currents in a bipolar arrangement, or each can be connected to the same terminal in a monopolar arrangement, with a neutral plate connected to the patient. This bipolar scheme intended for surface tissue treatments differs from the bipolar electrode described in U.S. Pat. No. 6,432,105B1 in that the two dome or ball shaped electrode electrodes are completely physically separated and are spaced apart a distance preventing significant discharges between them. For all practical purposes, the two electrodes operate independently and spread the RF energy over a wider area to reduce the possibility of burns.

Among other advantages, this feature also offers the cosmetic doctor the option of using the dual monopolar RF non ablative dome or ball probe for reaching and affecting deeper fat which typically penetrates about 20 mm, or the two dome or ball probes connected in a bipolar arrangement which will be effective mainly for superficial fat penetrating only 2 or 3 mm, both arrangements providing non-ablative contraction of collagen. This provides where desired a novel combination of RF monopolar and bipolar action in one cost effective RF handpiece which is a significant technological advance.

In accordance with a further feature of the invention, means are included within the handpiece to sense and display for the user the patient's skin temperature during treatment. In a further feature, the skin temperature can also be displayed on the electrosurgical generator front panel. In accordance with still a further feature of the invention, means are included within the handpiece to sense and display for the user the temperature of the electrode as a further way to prevent burns, as there may be a time lag between the electrode temperature and the skin temperature.

It is also possible within the scope of the invention to use a signal generated by the temperature sensing circuit to control the power applied to the handpiece and to its electrodes. This feature when combined with dual ball handpiece provides additional protection against possible damage to the skin tissue.

The four features described in the prior application: pre-applying to the skin a thermal gel, a known thermally and electrically-conductive material; using low radio-frequency power; relying on the natural cooling provided by a highly conductive electrode material; and continuously moving the electrode while in contact with the skin, should also be employed for the reasons described in the prior application.

As still a further feature of the invention, the handpiece is provided with means for maintaining the skin-touching active part of the electrode in continuous motion, and the tip of the electrode is itself made movable to more easily move the active electrode part over the contours of the skin, face, neck, etc.

It is believed that the RF technology produces an electric current that generates heat through resistance in the dermis and subcutaneous tissue. The thermal effect depends on the conductivity features of the treated tissue. Collagen fibrils, when heated, will denature and contract, which is believed to lead to the observed tissue tightening. Non-ablative RF treatment has a lower risk of complications, shorter recovery time and less disruption of regular activities.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention, like reference numerals designating the same or similar elements.

DETAILED DESCRIPTION OF PREFERRED EMBODIMENTS

Figure 1:
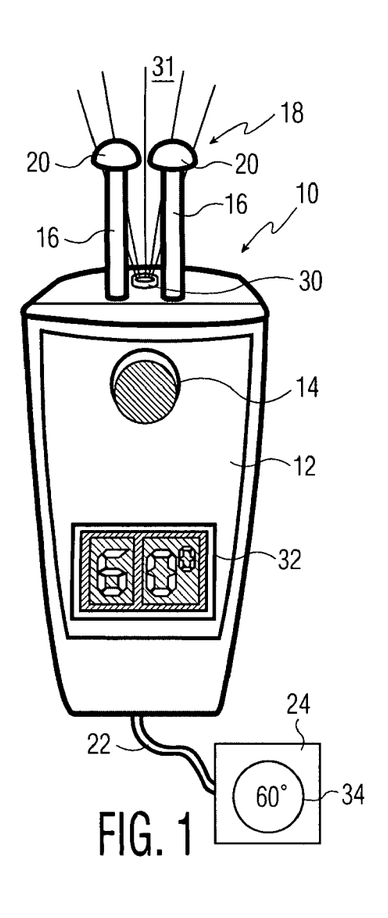
FIG. 1 is a plan view of one form of a handpiece with dual dome electrodes according to the invention, also illustrating one form of the temperature sensor feature of the invention.
Figure 13:
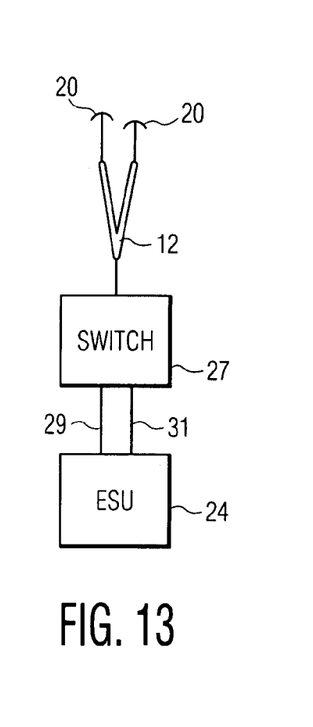
FIG. 13 is a schematic view and block diagram of a dual dome electrode connected to a switch and an electrosurgical unit.

In the present application, FIG. 1 is a schematic view of one form of RF applying device 10 in accordance with the invention. It comprises a handle or handpiece 12 with an operating button 14 and with a front end adapted to receive and hold rigidly the shank ends 16 of dual electrodes 18 whose working ends 20 are dome-shaped as shown. The handpiece 12 is electrically-insulating or if conductive is covered with an electrically-insulating coating. Similarly, the electrode's visible elongated shank 16 is partly coated with an electrically-insulating coating leaving bare the shank end for electrically-conductive engagement with the handle or handpiece and the active dome-shaped working ends 20 at the working end. The electrode 16 shank may be made long enough to be applied by the surgeon so as to readily contact any surface region of exposed skin of the patient's head or neck, typically the sites where skin treatments are desired. At the bottom end of the handle 12 is a cable 22 which contains two insulated wires for receiving bipolar or monopolar RF currents from a conventional RF electrosurgical generator unit (ESU) 24 shown schematically. As illustrated in the FIG. 2 interior view, the cable 22 is separately connected to the two dome-shaped sections by separate feed wires 26 in the handpiece 12. Each dome-shaped working end 20 can be connected to one of the two terminals of the source electrosurgical currents in a bipolar arrangement, or each can be connected to the same terminal in a monopolar arrangement, with a neutral plate (not shown) connected to the patient. The two dome or ball shaped electrodes are completely physically separated and are spaced apart a distance preventing significant discharges between them. For all practical purposes, the two electrodes operate independently and spread the RF energy over a wider area to reduce the possibility of burns. If desired, a switch 27 (FIG. 13) can be provided separately, or added to the handpiece if desired, to enable the user to switch the dome electrodes from the bipolar to the monopolar arrangement to control the depth of the tissue heating. In its simplest arrangement, the switch would be connected by separate cables 29, 31 to the ESU, one of which is plugged into the conventional monopolar connector on the electrosurgical unit 24 and the other of which is plugged into the bipolar connector of the electrosurgical unit. The switch can be operated by the surgeon as desired to supply either monopolar or bipolar RF energy to each of the dome-shaped working ends 20.

As a further feature of the invention, an infra-red (IR) sensor is added to the handpiece which is provided with a lens 30 to focus radiation 31 from the skin of the patient onto a known IR sensor for indicating skin temperature. The sensed temperature is displayed on a display 32 on the handpiece 12. If desired, the sensed temperature can also be displayed on a display 34 on the front panel of the ESU 24.

Figure 2:
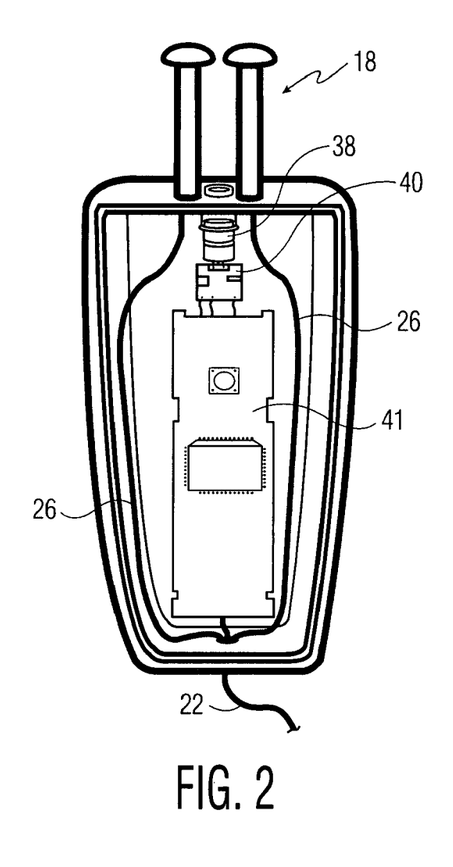
FIG. 2 is a plan view of the interior of the handpiece with dual dome electrodes as shown in FIG. 1.
Figure 4:
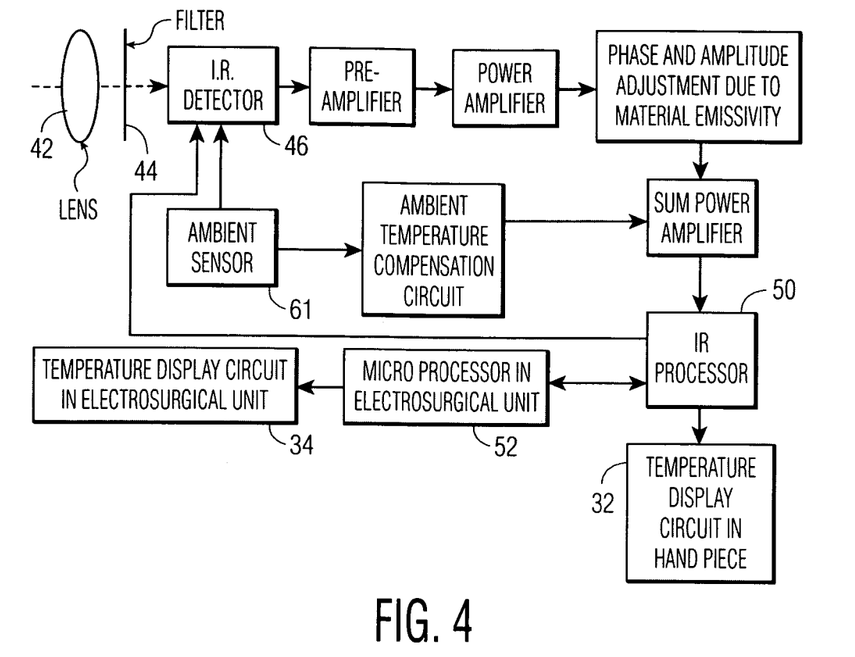
FIG. 4 is a circuit schematic of one form of single temperature sensor in accordance with the invention.

FIG. 2 illustrates schematically the interior of the handpiece 12. The optics is indicated at 38, and the IR sensor at 40, connected to a circuit board 41 containing an IR microprocessor and the remainder of the circuit used to measure and display the temperature. These circuits are well known in the art and commercially available. A typical circuit schematic is illustrated in FIG. 4. The optics includes a lens 42, and a filter 44 to filter out ambient radiation. The filtered radiation is detected by an IR detector 46, subsequently amplified and adjusted and compensated as illustrated and the result sent to an IR processor 50 which in turn displays the measured temperature on the handpiece display 32 and also optionally sends the information to the ESU processor 52 which in turn may display 34 the temperature on the ESU 24.

Figure 5:
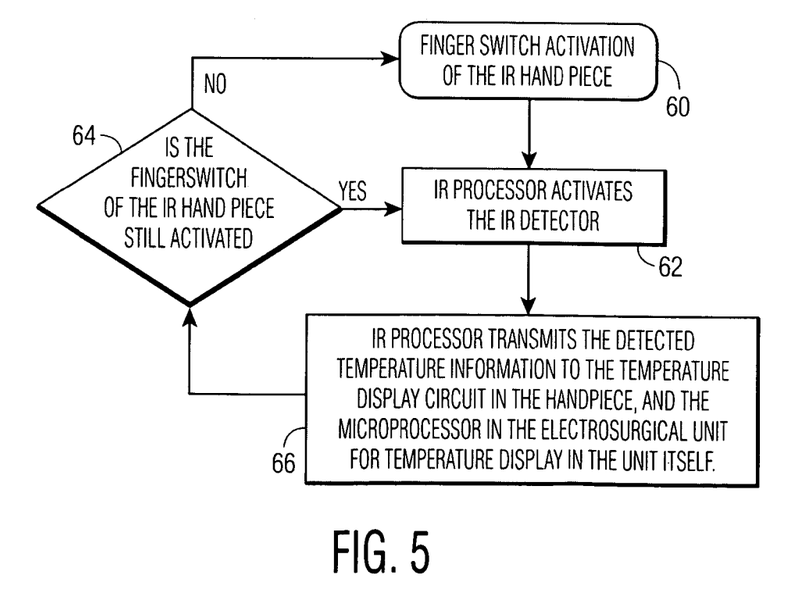
FIG. 5 is a typical flow chart for operating the single temperature sensor of FIG. 4.
Figure 6:
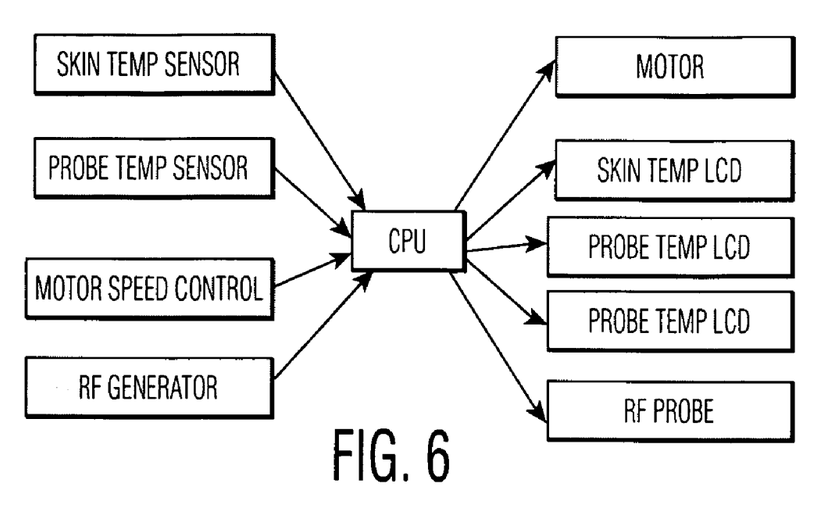
FIG. 6 is a block diagram of one form of dual temperature sensor for a handpiece in accordance with the invention.

Software in the IR processor 50 or ESU processor 52 may be used to control the operation. A typical software flow chart is illustrated in FIG. 5, and starts with activation 60 of the handpiece 12 which then activates the IR detector and circuitry 62. The software may include an activating button loop 64, and the actions described above are carried out as indicated in block 66.

Figure 3:
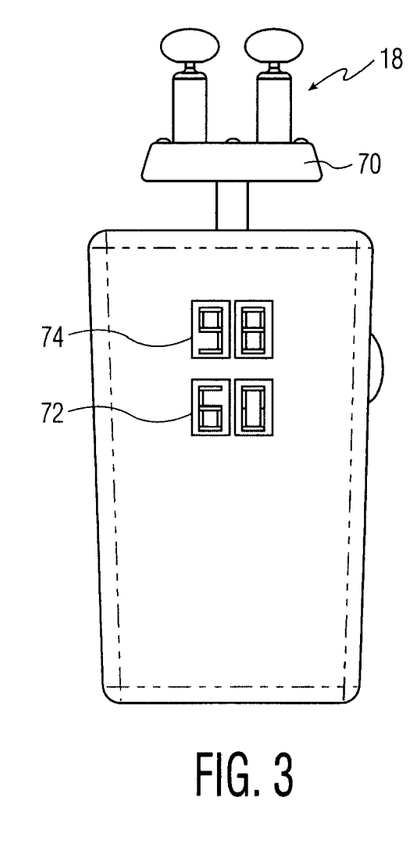
FIG. 3 is a plan view of another form of dual dome electrode according to the invention with dual sensors for the skin and electrode temperatures.

FIG. 3 illustrates a modification in accordance with the invention wherein both the skin temperature and the electrode temperature are measured as additional protection against an inadvertent burn. In this embodiment, the dual dome electrodes 18 are mounted on a block 70 which contains part or all of the IR circuitry, and the handpiece housing contains dual displays for the two measured temperatures. In this instance, the lower display 72 displays the dome temperature and the upper display 74 displays the skin temperature. The temperature values indicated are for illustrative purposes only.

Figure 7:
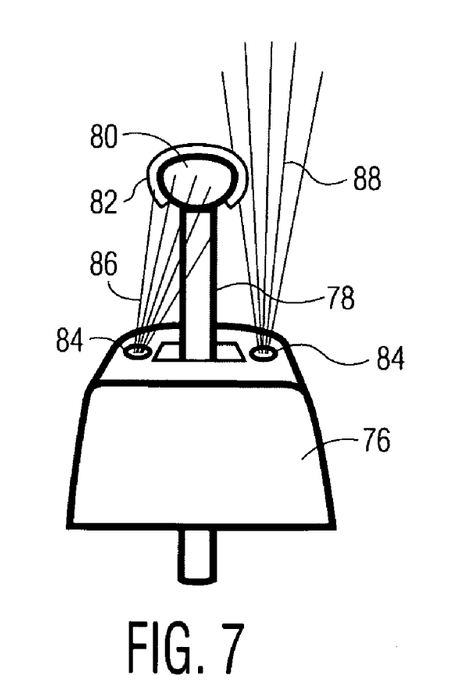
FIG. 7 illustrates one way in which the handpiece can receive radiation from the skin and electrode.
Figure 8:
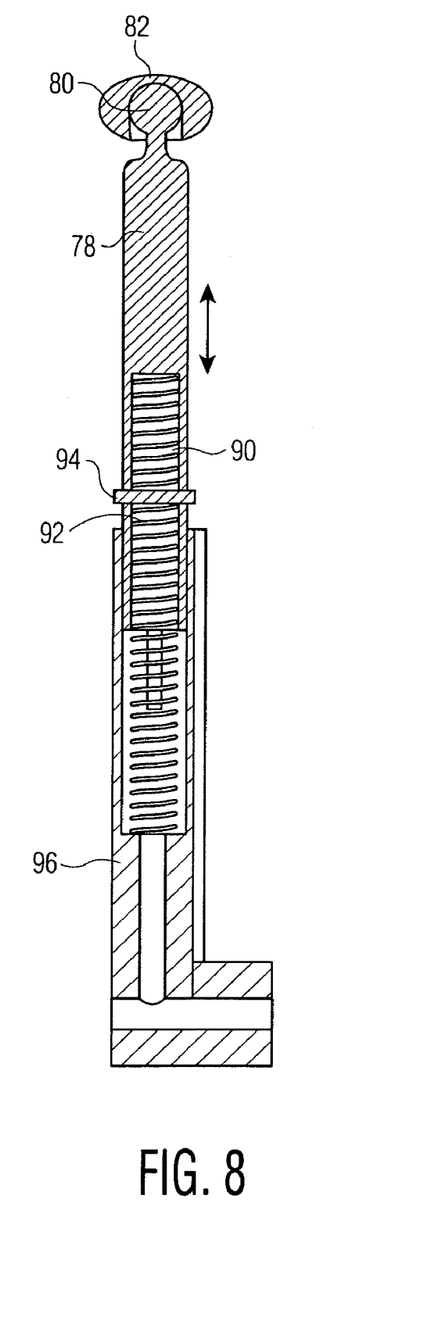
FIG. 8 is cross-sectional view of one form of the movable electrode for a handpiece in accordance with the invention.
Figure 9:
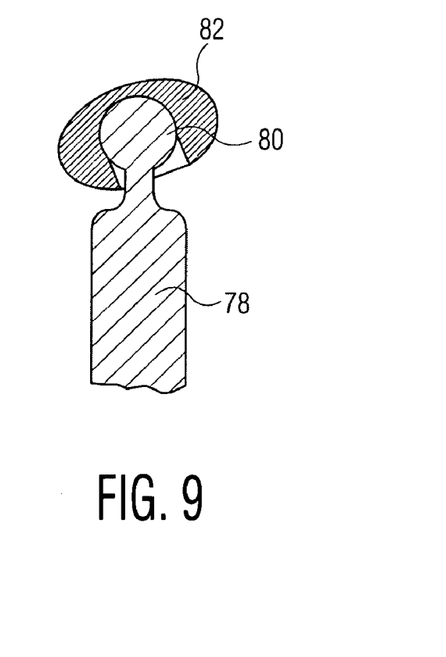
FIG. 9 illustrates how the electrode tip can be made movable.

While FIG. 3 illustrates the dual sensor feature of the invention with dual electrodes, it will be understood that the dual sensor feature can also be employed with only one electrode, which is illustrated in FIG. 7, which only shows the upper part 76 of the handpiece. The electrode is shown at 78 and comprises a dome active end 80 covered by a generally oval-shaped cap 82 which clamps on over the dome and can roll around over the dome 80, which is illustrated in FIG. 9. Items 84 are lenses, the left one of which is focused on electrode 80 and collects IR radiation from the latter, indicated at 86, and the right one of which is focused on the patient's skin and collects IR radiation from the latter, indicated at 88. Individual IR processing circuits as shown in FIG. 4 can be used for each of the radiations, or a common known multiplexing circuit can be used to process sequentially the electrode and skin IR signals. The movable cap 82 moves like a roller around the dome 80 and makes it easier to move working electrode surface along the contours of the face and neck, for example. This is aided by an up and down movement of the working electrode end, which can be achieved by the construction illustrated in FIG. 8 as an example. The electrode shank 78 has a hollow section 90 in which a compression spring 92 is mounted and allows the shank 78 to move up and down as indicated by the arrow and limited by a stop 94 in response to the movements by the user.

Figure 10:
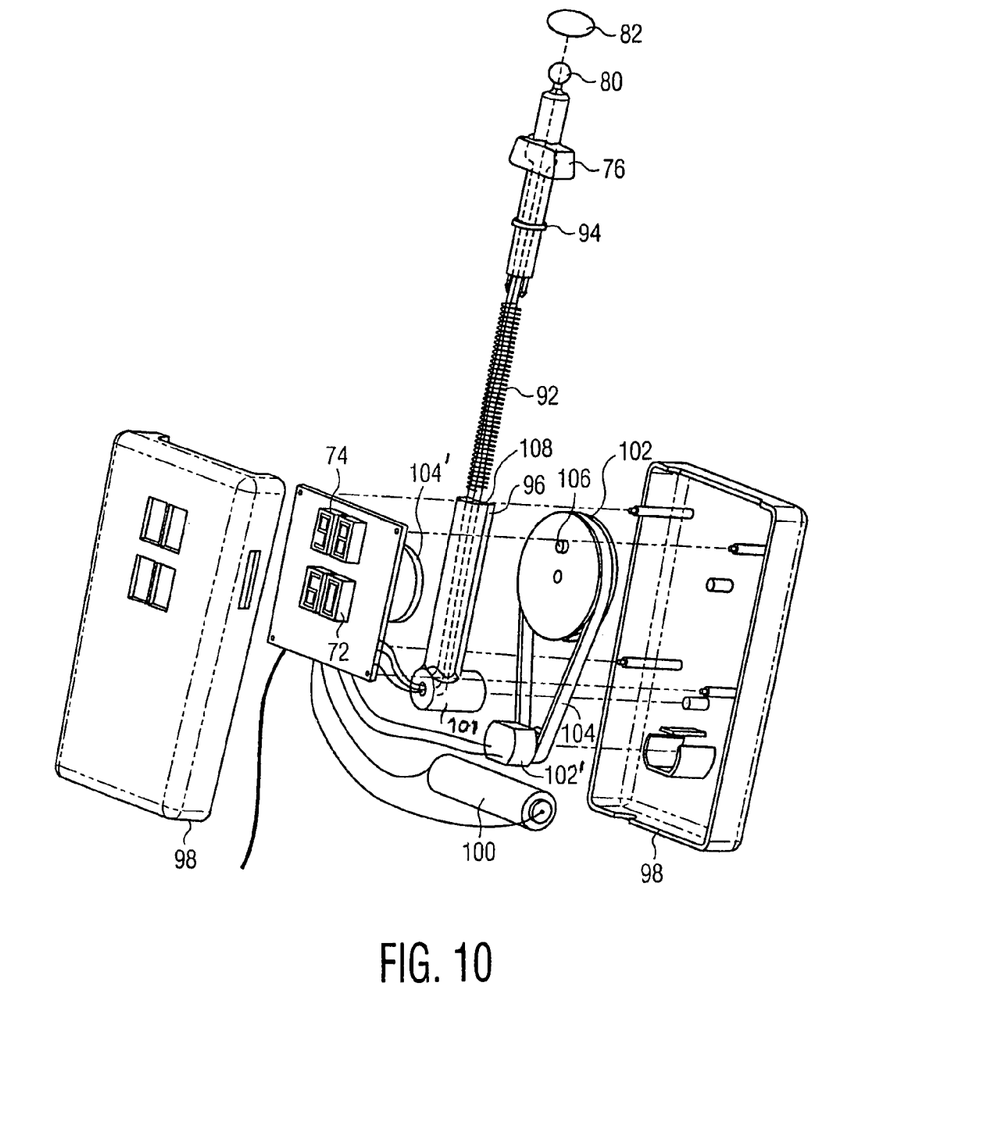
FIG. 10 is an exploded view of a handpiece in accordance with the invention with a motor driven electrode for maintaining the electrode continuously in motion.
Figure 11:
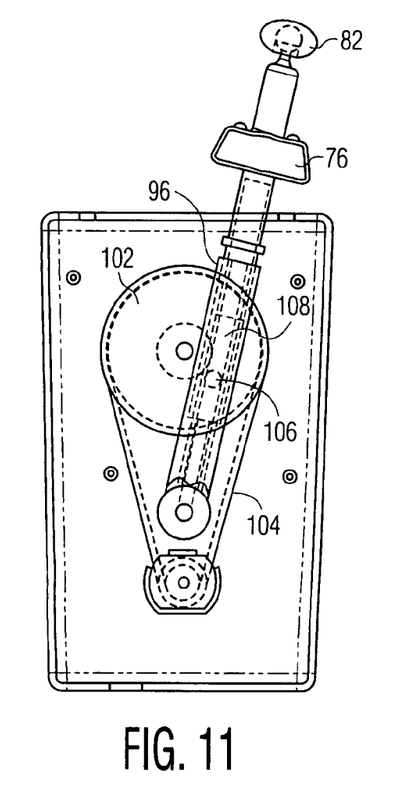
FIGS. 11 and 12 schematically illustrate the extreme positions assumed by the electrode during operation.
Figure 12:
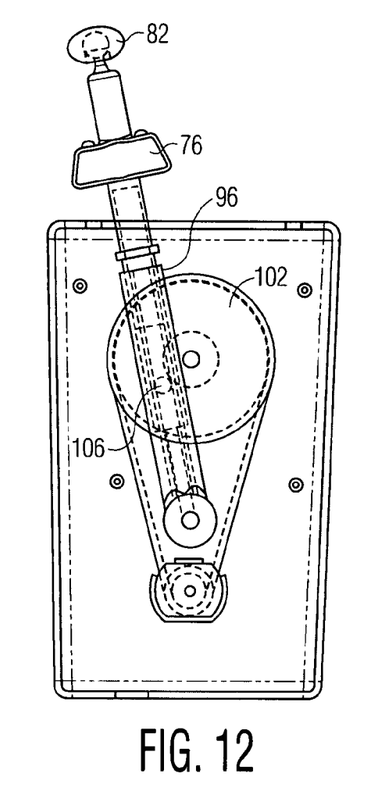

The compression spring assembly is mounted on an arm 96 which as a further feature of the invention, illustrated in the exploded view in FIG. 10, provides oscillations of the active electrode end moving sideways back and forth either under manual or motorized control illustrated in the figure. The movable assembly is housed in a case 98 which includes a battery 100 connected to a motor 102' via a conventional motor control circuit (not shown) and the up-down actuator 101. The battery 100 drives a pulley 102 with a belt 104. The pulley pivots on a pin in the bottom housing half. A pin 106 is located on the pulley, and a slot 108 is located on the back of the arm 96. The pin 106 rides in the slot 108. The arm 96 also pivots about a pin on the bottom housing half. As the pulley 102 rotates, the pulley pin 106 causes the arm 96 to oscillate back and forth as the pulley pin rides in the slot 108. This is similar to a known pin and slot mechanism for converting rotary into lateral motion. The extreme positions of the active electrode cap 82 are shown in FIG. 11 (the electrode at the right) and FIG. 12 (the electrode at the left). A typical side-to-side movement is about 1-2 inches. The oscillation speed is dictated by the motor speed, which can be controlled by the user via the speed adjustment wheel 104'. For this purpose, controlling the motor voltage may be sufficient to vary the oscillation from 0 to 100 Hz. Oscillation at the lower end of the range is preferred. A more sophisticated arrangement may be provided by the use of known motor control IC chips, which typically rely on pulse code modulation to vary the motor speed. The unit can also be powered by an outside AC power source if desired.

The combination of the up and down motion (FIG. 8), the side-to-side motion (FIG. 10), and the roller motion (FIG. 9) of the cap during the procedure assist in maintaining constant electrode motion thereby reducing the chance of inadvertent burns to the patient and allow the electrode to follow closely the skin contour. Preferably, the oscillations are started first before the RF energy is applied. Concerning the IR sensor readings, it has been shown that one sensor can be used with and for one electrode, two sensors can be used with and for one electrode and the skin, and one sensor can be used with two electrodes, from which it will be evident that two sensors can be used with two electrodes (each sensing one of the electrode's temperature), and three sensors can be used if desired with the two electrodes with the third sensor reading skin temperature.

Once the surgeon has positioned the working end 20 of the instrument with respect to the tissue to be operated on, he or she then activates the radio-frequency apparatus 24 causing a electrosurgical RF currents to flow between the bare electrodes 20 and the underlying tissue capable of causing heating of tissue as was described above. Other usable mechanical or electrical structures following the teachings of the prior patent will be appreciated by those skilled in this art.

Reduced uniformity of the RF energy over the surface area may cause charges to concentrate in specific regions of the electrodes, and could cause an unintentional burn to the patient. The curvature and increased uniformity of the dome shaped electrodes (10 mm is a typical diameter) with smooth edges (no sharp edges where RF power can concentrate) leads to more uniform RF energy over the whole surface area and hence is safer for the non-ablative skin tightening method.

A feature of the present invention is to minimize the possibility of harm to the patient's skin during a cosmetic procedure by measuring the skin temperature during the procedure using an IR sensor in the handpiece in a position to receive IR emitted by the heated skin surface. The emitted IR can be received via an aperture in the front end of the handpiece and focused by a lens through a filter onto the IR detector. Generally speaking, the IR detector converts the detected radiation into a voltage signal, which is then amplified, compared, corrected and displayed in a temperature display located both on the handpiece and on the front panel of electrosurgical generator. The signal, whose intensity is related to the temperature, can also be used to provide safety backup during the procedure. For example, if the voltage level is too high, representing a high skin temperature, the signal inputted to the microprocessor 52 can be used to either reduce the power output or even shut off the RF power. This is easily handled by the already present microprocessor in the ESU.

There are many known ways to measure temperature using emitted IR from a target. The present invention is not directed to how temperature is measured but rather how it is used in a RF cosmetic procedure. For completeness' sake, an IR measuring circuit as described in for example U.S. Pat. No. 4,784,149 can be used. The principle is well known. Infrared radiation emitted by tissue surfaces is collected by an infrared lens 42 (FIG. 4) and focused onto an infrared sensor 46. The infrared sensor 46 generates a signal voltage dependent on the temperature difference between the body tissue being observed and the infrared sensor. To determine the true tissue temperature, an additional sensor 61 is used to measure the ambient temperature of the infrared sensor 46 and this ambient temperature is added to the signal voltage. The relationship between the signals to generate accurate tissue temperature can be expressed in a formula that can easily be computed by a microprocessor. The ambient sensor 61 may be a linear semiconductor device which generates a current proportional to its temperature. This sensor is attached to the infrared radiation sensor 46 for accurate tracking of the ambient temperature of the infrared sensor. The signal from the ambient sensor is added to that of the infrared sensor by means of a well known summing amplifier. Various well known schemes can be included to calibrate the sensing mechanism for more accurate results if desired. In this application, extreme accuracy is unnecessary because there is a reasonable range of temperatures within which collagen tissue can be affected before burning of the ski occurs. In addition, extreme skin temperatures will be sensed by the patient who can be counted on to inform the surgeon. The entire measuring cycle is very quick, and so almost instantaneous skin temperatures will be displayed both on the handpiece display and on generator.

As described in the referenced co-pending application, the electrode is always moved continuously back and forth over the patient's skin which prevents one skin area from being exposed continuously to the RF currents. In addition, the surgeon can use the displayed temperature to control the power transmitted to the electrode. In other words, the surgeon can apply the power intermittently as he/she monitors the display and the skin area being treated.

By employing a second IR sensor focused on the electrode and therefore displays the electrode temperature in a separate display in addition to the skin temperature, an additional level of protection against inadvertent burns is provided as the surgeon monitors the electrode temperature.

The preferred metal for the working end of the electrode is a highly electrically-conductive and thermally conductive material, a silver alloy being preferred.

The radio-frequency apparatus used outputted high frequency (RF) radio-frequency currents in the range of about 3.8-4.0 MHz. Continuous wave power can be used. The electrode compositions described in our copending application Ser. No. 11/180,809, filed Jul. 14, 2006, the contents of which are herein incorporated by reference, are deemed suitable for this application with the solid electrode rather than the laminated coated electrode being preferred. In general, the silver alloy preferably has a content by weight of about 93-98% by weight silver with about 1.5-4% by weight of germanium and 1-2% by weight of indium. A preferred composition is 97% silver with 2% germanium and 1% indium.

A wide variety of conductive topical gels, which are also referred to as thermal gels, can be used. This helps spread the heat uniformly over the skin surface. It may be desirable to also use chilling at the end of each skin section treatment. For example, following the heating of a skin section for several minutes, when the skin temperature has reached a certain value of about 44° C., then cool gels, commercially available, can be applied to the heated section to quickly cool it down to room temperature and thus stabilize the collagen structure.

In summary, radiofrequency skin tightening is a new and very promising tool for the non-surgical tightening of loose or sagging skin. Most patients will see at least a mild improvement, with minimal downtime and minimal risk. The 3.8-4 MHz radio-frequency unit appears well suited for non-ablative in-office rejuvenation of the skin and provides a measurable improvement in the majority of patients treated. This procedure is believed to be an effective, non-invasive, economical and safe tool. In addition, costs connected to this new method are rather low, and even less skilled professionals can be easily trained on this technology, thanks to the low risks that its use involves.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A device for use in a surgical procedure for improving the appearance of skin tissue of a patient by applying RF energy thereto, the device comprising a handpiece for receiving radio-frequency currents from a generator, the handpiece comprising:
    (a) a first member having a first end and a distal second end,
    (b) an electrosurgical dome-shaped electrode mounted at and extending from the second end of the first member,
    (c) at least a first electrically-conductive wire at the first end and extending through the first member for applying to the electrode at the second end a radio-frequency voltage capable of generating radio-frequency currents to activate the electrode,
    (d) means for allowing a side to side motion of the electrode relative to the first member
    (e) further comprising motor means for causing the electrode to swing from side to side.

2. A device as claimed in claim 1, wherein the side to side motion covers a distance of 1-2 inches.

* * * * *